United States Patent [19]

Boyle et al.

[11] Patent Number: 4,695,574
[45] Date of Patent: Sep. 22, 1987

[54] 4-QUINOLINYLAMINO-N-[PYRROLIDINYL OR PIPERDINYL)ALKYL]-BENZENESULPHONAMIDES

[75] Inventors: John T. A. Boyle, Cookham; Richard S. Todd, Near Slough, both of England

[73] Assignee: American Home Products Corporation, New York, N.Y.

[21] Appl. No.: 809,996

[22] Filed: Dec. 17, 1985

[30] Foreign Application Priority Data

Dec. 19, 1984 [GB] United Kingdom ............... 8432091

[51] Int. Cl.$^4$ .................. C07D 215/44; A61K 31/47
[52] U.S. Cl. .................................. 514/313; 546/160
[58] Field of Search ..................... 546/160; 514/313

[56] References Cited

U.S. PATENT DOCUMENTS 3,933,829  1/1976  Archibald et al. ............... 546/160

FOREIGN PATENT DOCUMENTS 1445595  8/1976  United Kingdom .

Primary Examiner—Jane T. Fan
Attorney, Agent, or Firm—Arthur G. Seifert

[57] ABSTRACT

4-Aminoquioline derivatives having the formula

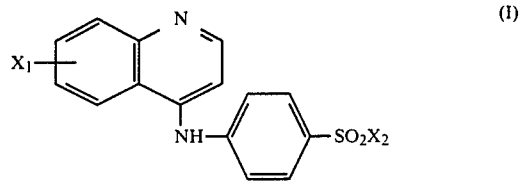

(I)

and their pharmaceutically acceptable salts where $X_1$ is halogen or trifluoromethyl and $X_2$ is a group having the formula

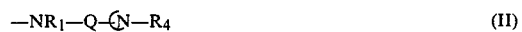

(II)

where $R_1$ is hydrogen or lower alkyl; Q is lower alkylene; $R_4$ is lower alkyl and the ring illustrated is a piperidine or pyrrolidine ring optionally substituted by lower alkyl, exhibit anti-hypertensive activity. Corresponding compounds where $R_4$ is replaced by latent lower alkyl, a protecting group or hydrogen may be used as intermediates.

11 Claims, No Drawings

4-QUINOLINYLAMINO-N-[PYRROLIDINYL OR PIPERDINYL)ALKYL]-BENZENESULPHONAMIDES

The present invention concerns new 4-aminoquinoline derivatives, a process for their preparation and pharmaceutical compositions containing them. The invention also relates to new benzenesulphonamide derivatives useful as intermediates for the preparation of the 4-aminoquinoline derivatives and processes for the preparation of the benzenesulphonamide derivatives.

British Patent No. 1,445,595 discloses a class of 4-aminoquinoline derivatives having anti-hypertensive activity. The compounds specifically disclosed include 4-(7-chloro-4-quinolinylamino)-N-(2-diethylaminoethyl)-benzenesulphonamide and 4-(7-chloro-4-quinolinylamino)-N-(1-ethyl-3-piperidyl)benzenesulphonamide. For short we shall refer to these compounds as compound A and compound B respectively.

In accordance with the present invention another class of 4-aminoquinoline derivatives have been found to be useful as anti-hypertensive agents. The 4-aminoquinoline derivative of the invention closest in structure to compounds A and B is compared with compounds A and B in the pharmacological results herein.

The invention provides novel 4-aminoquinoline derivatives having the formula I

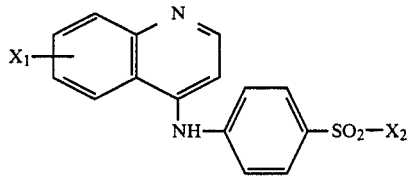

and their pharmaceutically acceptable salts, wherein $X_1$ is halogen or trifluoromethyl and $X_2$ represents a group having the formula II

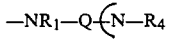

wherein Q is lower alkylene attached to a ring carbon atom of the ring illustrated in formula II, $R_1$ is hydrogen or lower alkyl; $R_4$ is lower alkyl and the ring illustrated in formula II is a piperidine or pyrrolidine ring that may be substituted on one or more carbon ring members by lower alkyl. These compounds are indicated for pharmaceutical use, particularly as anti-hypertensive agents.

It will be apparent to those skilled in the art that the above definition of $X_2$ includes moieties possessing an asymmetric carbon atom, especially, for instance, where the group having the formula III

is 1-(lower alkyl)-2 or 3-pyrrolidinyl or 1-(lower alkyl)-2 or 3- piperidyl. It is to be understood that formula I is intended to encompass each enantiomer where the compound contains an asymmetric carbon atom and mixtures of enantiomers, for instance, a racemic mixture of enantiomers. Separation of enantiomers can be carried out using general methods known in the literature.

$X_1$ in formula I may substitute any of the 5, 6, 7 and 8- positions of the quinoline ring system, but is preferably at the 7- or 8- position, advantageously the 7- position. Where $X_1$ is at the 7- position, formula I may be represented as Ia

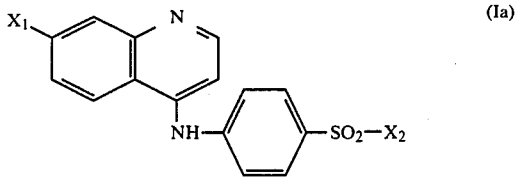

$X_1$ represents halogen, for instance, chlorine or bromine, or trifluoromethyl. $X_1$ is preferably chlorine.

In formula II $R_1$ represents hydrogen or lower alkyl (for instance methyl, ethyl, propyl, butyl). $R_1$ is preferably halogen. In formula II, Q is lower alkylene which may be a straight chain, i.e. a chain of 1 to 6, preferably 1 to 4, methylene groups. Alternatively Q may be a branched lower alkylene group, for instance, a chain of 1 to 4 methylene groups, the chain being mono- or di-substituted by methyl or monosubstituted by ethyl. Q is preferably methylene or substituted methylene. Q is attached to the ring shown in formula II via a ring carbon atom not the ring nitrogen atom. Q is preferably attached to carbon ring member that is itself attached to the ring nitrogen atom. $R_4$ in formula II is lower alkyl (for instance methyl, ethyl, propyl or butyl). The ring attached to Q in formula II is a piperidine or pyrrolidine ring whose nitrogen atom is shown in the formula. The ring may be substituted on one or more ring carbon atoms by lower alkyl (for instance methyl, ethyl, propyl, butyl). The ring carbon atoms are preferably unsubstituted except, of course, by the lower alkylene group Q.

Advantageously $X_2$ is a group having the formula

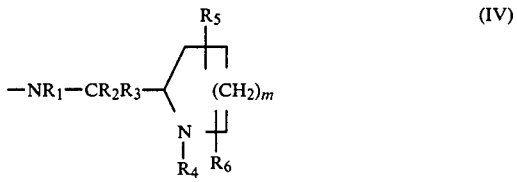

wherein $R_1$ and $R_4$ are as defined above; $R_2$, $R_3$, $R_5$ and $R_6$ are independently selected from hydrogen and lower alkyl; $R_5$ and $R_6$ are each attached to a ring member other than nitrogen and m is 0 or 1.

The term "lower" as used herein to refer to such groups as alkyl, alkoxy and alkylene, indicates that the group contains up to 6, preferably up to 4, carbon atoms. In the case of "lower alkanoyl" the group contains 1 to 6, preferably 1 to 4 carbon atoms. The group may be in the form of a straight chain or may be branched.

The compounds having formula I form acid addition salts with acids. Examples of acid addition salts are those formed from inorganic and organic acids and in particular include the sulphate, hydrochloride, hydrobromide, hydroiodide, nitrate, phosphate, sulphonates (for instance the methanesulphonate or p-toluenesulphonate), acetate, maleate, fumarate, tartrate, malonate, citrate and formate.

As illustrative compounds of the invention there may be mentioned, in the case of formula I, 4-(7-chloro-4-quinolinylamino)-N-[(1-ethyl-2-piperidinyl)methyl]benzenesulphonamide; 4-(7-chloro-4-quinolinylamino)-N-

(1-propyl-2-pyrrolidinyl)methyl]benzenesulphonamide; 4-(7-chloro-4-quinolinylamino)-N-[(1-butyl-2-pyrrolidinyl)methyl]benzenesulphonamide; 4-(7-chloro-4-quinolinylamino)-N-[(1-methyl-2-pyrrolidinyl)]-benzenesulphonamide and N-[(1-ethyl-2-pyrrolidinyl)-methyl]-4-(7-trifluoromethyl-4-quinolinylamino)benzenesulphonamide and their pharmaceutically acceptable acid addition salts.

The invention also provides novel compounds having the formula V

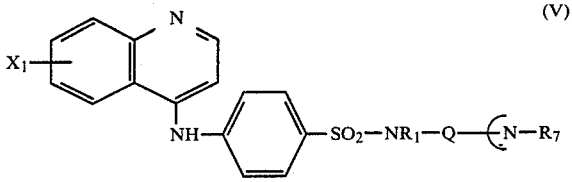

and their acid addition salts (wherein $X_1$ is as defined under formula 1; $R_1$, Q and the ring attached to Q are as defined under formula II and $R_7$ is selected from latent lower alkyl, a protecting group and hydrogen. $R_7$ is preferably lower alkanoyl or hydrogen. The compounds having formula V and their salts are indicated for use as chemical intermediates for the preparation of the compounds having formula I and their pharmaceutically acceptable acid addition salts.

Examples of compounds of the invention include, in the case of formula V, N-[(1-acetyl-2-pyrrolidinyl) methyl]-4-(7-chloro-4-quinolinylamino)benzenesulphonamide and N-[(1-benzyl-2-pyrrolidinyl)methyl]-4-(7-chloro-4-quinolinyl)benzenesulphonamide and their acid addition salts.

The compounds having formula I may be made by (a) sulphonylation of a compound having the formula $X_2H$ (where X is as defined above) or a salt thereof to introduce a sulphonyl group having the formula VII

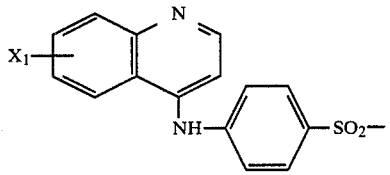

(where $X_1$ is as defined above);

(b) reaction of a compound having the formula VIII

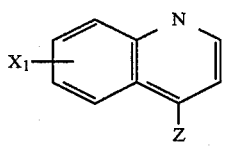

(where $X_1$ is as defined above and Z is a leaving group or atom, preferably halogen such as chlorine) with a compound having the formula IX

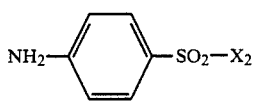

(where $X_2$ is as defined above) or a salt thereof; or (c) alkylation of a sulphonamide having the formula

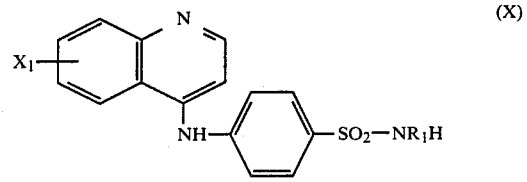

(where $X_1$ and $R_1$ are as defined above) under alkaline conditions to introduce the substituted alkyl group having the formula

(where Q, the ring to which Q is attached and $R_4$ are as defined under formula II) at the sulphonamide nitrogen atom; or (d) alkylating compound having the formula V as defined and illustrated above in which $R_7$ is hydrogen to introduce a lower alkyl group as $R_4$; or (e) converting latent lower alkyl in a compound of formula V in which $R_7$ is latent lower alkyl into lower alkyl.

If desired the process of preparation of the compound having formula I or salt thereof may include conversion of a salt of a compound having formula I into a compound having formula I or conversion of a compound having formula I into a salt thereof.

The compounds having formula V where $R_7$ is latent lower alkyl or a protecting group may be prepared in a similar manner to those of formula I (except that step (d) is not used) by replacing $R_4$ by latent lower alkyl or a protecting group. Compounds having formula V in which $R_7$ is hydrogen may be prepared by removing the protecting group in known manner from a compound having formula V in which $R_7$ is a protecting group.

The intermediate compounds useful for preparation of the compounds having formulae I and V are generally known or may be prepared in known manner. Compounds having formula IX are described in British Patent Application No. 8514648.

As sulphonylating agent in step (a) there is preferably used the sulphonyl chloride having the formula W-Cl where $W_1$ is the sulphonyl group having the formula VII. The sulphonylation may be carried out in manner known for the sulphonylation of ammonia and amines. The sulphonylation may be performed in a solvent, for instance, chloroform or methylene chloride, in the presence of a base to neutralise the hydrogen chloride formed. The base may be inorganic, for instance, an alkali metal carbonate or bicarbonate or may be an organic base, particularly one that is inert towards sulphonylating agent, for instance, a tertiary amine such as triethylamine, or an excess of the amine to be sulphonylated.

The intermediate sulphonamides having formula V and their salts in which $R_8$ is latent lower alkyl may be converted into the sulphonamides having formula I and their salts via step (e) in which the latent lower alkyl group is converted to lower alkyl. The latent lower alkyl group is preferably lower alkanoyl. The conversion of the lower alkanoyl group $R_8$ into the lower alkyl group $R_4$, for instance, acetyl into ethyl, may be carried out in known manner for the reduction of amides to form amines. Where $X_1$ is halogen such as chlorine in formula V, the reduction conditions should be chosen so as to avoid replacement of $X_1$ by hydrogen. As reducing agents alane and borane may be used. Lithium aluminium hydride may be used as reducing agent where $X_1$ is trifluoromethyl.

Alkylation according to step (d) may be carried out in manner known for the alkylation of amines. As alkylating agent there may be used a compound having the formula $R_4$-Z where Z is a leaving group or atom, preferably halogen, for instance chlorine or bromine or organosulphonyloxy, for instance, lower alkanesulphonyloxy or tosyloxy.

Step (b) is a reaction that is preferably carried out in aqueous alcohol. The reaction may be carried out with or without acid catalysis In step (c) the sulphonamide X is alkylated under alkaline conditions to introduce the substituted alkyl group having the formula XI. As substituted alkylating agent there may be used a compound having the formula W-Z where Z is as defined above and W represents the substituted alkyl group Xi. The reaction may be carried out in known manner for the alkylation of sulphonamide nitrogen atoms. The compounds having the formula W-Z are generally known, for instance 2-chloromethyl-1-ethyl-piperidine, or may be prepared by known methods. The alkaline conditions used for the reaction may be provided by converting the sulphonamide into an alkali metal salt thereof prior to adding the substituted alkylating agent.

The novel compounds having formula I and their pharmaceutically acceptable salts are indicated for use as anti-hypertensive agents, the compounds may be tested for their response on the blood pressure of spontaneously hypertensive rats in the following procedure:

The blood pressure of male or femal conscious rats that are spontaneously hypertensive are measured in a 39° C. constant temperature housing by means of a tail cuff. Rats with systolic pressures below 155mm Hg are not used. Groups of rats (4 per group) are dosed orally with the test substance in a suitable vehicle or with vehicle alone. Systolic pressures are recorded before dosing and at selected time points afterwards (2 hours, 6 hours and 24 hours).

The compound of the invention according to Example 1 and the known 4-aminoquinoline derivatives referred to above as compound A and compound B have been tested in the above procedure with the results given below in Table 1 at a dose of 0.03 millimoles/kg p.o. and the results given below in Table 2 at a dose of 0.003 millimoles/kg p.o.

TABLE 1

| Compound | Blood pressure as % of initial value after | | | Heart rate as % of initial value after | | |
|---|---|---|---|---|---|---|
| | 2 hours | 6 hours | 24 hours | 2 hours | 6 hours | 24 hours |
| Example 1 herein | 55 | 55 | 79 | 91 | 79 | 81 |
| Compound A | 79 | 73 | 67 | 72 | 70 | 66 |
| Compound B | 64 | 66 | 60 | 81 | 66 | 70 |

TABLE 2

| Compound | Blood pressure as % of initial value after | | | Heart rate as % of initial value after | | |
|---|---|---|---|---|---|---|
| | 2 hours | 6 hours | 24 hours | 2 hours | 6 hours | 24 hours |
| Example 1 herein | 74 | 51 | 69 | 104 | 102 | 87 |
| Compound A | 89 | 73 | 83 | 93 | 86 | 81 |
| Compound B | 97 | 91 | 97 | 95 | 85 | 95 |

At the higher dose tested (0.03 millimoles/kg) all three compounds were active in reducing blood pressure. The compound of the invention achieved the greatest reduction in blood pressure (a reduction of 55% of initial value). The compound of the invention also exhibited the advantage that it caused a smaller reduction in the heart rate than compound A and compound B at each of the three times of measurement.

At the lower dose tested (0.003 millimoles/kg) compound B showed little effect in reducing blood pressure. The compound of the invention and compound A were both active in reducing blood pressure. However, the compound of the invention caused a greater reduction in blood pressure than compound A at each of the three times of measurement. The compound of the invention also exhibited an advantage over compound A in that it caused a smaller reduction in heart rate at each of the three times tested.

Thus the compound of the invention is more active than compound A and compound B and also has the advantage of a lower reduction (or no reduction) in the heart rate.

The end compounds of the invention prepared in Examples 1 to 6 herein have been tested in the procedure given above at 0.03 millimoles/kg p.o. The results obtained are given in Table 3.

TABLE 3

| Compound (Example No) | Blood Pressure as % of initial value after | | | Heart rate as % of initial value after | | |
|---|---|---|---|---|---|---|
| | 2 hours | 6 hours | 24 hours | 2 hours | 6 hours | 24 hours |
| 1 | 55 | 55 | 79 | 91 | 79 | 81 |
| 2 | 58 | 52 | 73 | 92 | 90 | 87 |
| 3 | 53 | 57 | 65 | 80 | 78 | 73 |
| 4 | 63 | 56 | 92 | 93 | 95 | 93 |
| 5 | 50 | 54 | 68 | 79 | 84 | 83 |
| 6 | 56 | 58 | 76 | 88 | 81 | 76 |

When a compound having formula I or V or a salt thereof contains an asymmetric carbon atom, the compound may exist in the form of an individual enantiomer or a mixture of enantiomers, for instance, a racemic mixture. Individual enantiomers may be prepared by using an optically active starting material, for instance, as in Example 5 or 6, or by separating a mixture of enantiomers, for instance, a racemic mixture using known methods of separation.

The invention also provides a pharmaceutical composition comprising a compound having formula I or a pharmaceutically acceptable acid addition salt thereof in association or combination with a pharmaceutically acceptable carrier. Any suitable carrier known in the art can be used to prepare the pharmaceutical composition. In such a composition, the carrier is generally a solid or liquid or a mixture of a solid and a liquid.

Solid form compositions include powders, granules, tablets, capsules (e.g. hard and soft gelatin capsules), suppositories and pessaries. A solid carrier can be, for example, one or more substances which may also act as flavouring agents, lubricants, solubilisers, suspending agents, fillers, glidants, compression aides, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99% e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils and fats. The liquid carrier can contain other suitable pharmaceutical additives such as solubilizers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycerol and glycols) and their derivatives and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form. The quantity of the active ingredient in unit dose of composition may be varied or adjusted from 0.5 mg to 750 mg, according to the particular need and the activity of the active ingredient. The invention also includes the compounds in the absence of the carrier where the compounds are in unit dosage form.

The invention is illustrated by the following examples:

EXAMPLE 1

4-(7-Chloro-4-quinolinylamino)-N-[(1-ethyl-2-pyrrolidinyl)-methyl]benzenesulphonamide 4-(7-Chloro-4-quinolinylamino)benzenesulphonyl chloride hydrochloride (23.4 g, 0.06 mol) was added portionwise to a well stirred mixture of aqueous sodium carbonate (60 g in 600 ml water) and 2-aminomethyl-1-ethyl pyrrolidine (7.8 g, 0.06 mol) in chloroform (600 ml) at about 10° C. The ice bath used for cooling was removed and, after 1½ hours, the mixture was filtered. The chloroform layer was separated and dried (MgSO$_4$). Concentration under reduced pressure caused precipitation of a solid, which was collected by filtration and dried. Recrystallisation from ethanol gave the title compound (10.5 g), melting point 200°–201.5° C.

Analysis: Found: C, 59.3%; H, 5.85%; N, 12.3%. $C_{22}H_{25}ClN_4O_2S$ requires C, 59.4%; H, 5.66%; N, 12.6%.

The title compound was dissolved in hot isopropanol and an ethereal solution of hydrogen chloride was added to give a precipitate of the title compound dihydrochloride hemihydrate ¾ isopropanolate, melting point 233°–237° C.

Analysis: Found: C, 51.1%; H, 6.02%; N, 9.68%. $C_{22}H_{25}ClN_4O_2S.2HCl.1/2H_2O.3/4C_3H_8O$ requires C, 50.9%; H, 5.99%; N, 9.80%.

EXAMPLE 2

4-(7-Chloro-4-quinolinylamino)-N-[(1-ethyl-2-piperidinyl)-methyl]benzenesulphonamide 4-(7-Chloro-4-quinolinylamino)benzenesulphenyl chloride hydrochloride (16.6 g, 0.017 mol) was added portionwise to a well stirred mixture of aqueous sodium carbonate (17 g in 200 ml water) and 2-aminomethyl-1-ethyl-piperidine hydrobromide (3.8 g, 0.017 mol) in chloroform (180 ml) at about 10° C. The ice bath used for cooling was removed. After 1½ hours, the mixture was filtered. The chloroform layer was separated, dried (MgSO$_4$) and evaporated under reduced pressure to give a gum. Crystallisation from ethanol gave the title compound (0.47 g), melting point 203°–205° C.

Analysis: Found: C, 60.1%; H, 5.87%; N, 12.1%. $C_{23}H_{25}ClN_4O_2S$ requires C, 60.2%; H, 5.49%; N, 12.2%.

EXAMPLE 3

4-(7-Trifluoromethyl-4-quinolinylamino)-N-[(1-ethyl-2-pyrrolidinyl) methyl]benzenesulphonamide 4-(7-Trifluoromethyl-4-quinolinylamino)benzenesulphonyl chloride hydrochloride (4.3 g, 0.01 mol) was added portionwise to a well stirred mixture of aqueous sodium carbonate (12.3 g in 70 ml of water) and 2-aminomethyl-1-ethylpyrrolidine (1.3 g, 0.01 mol) in chloroform (70 ml) at about 10° C. The ice bath used for cooling was removed and, after 1½ hours, the mixture was filtered. The solid was washed with water and then air-dried. Recrystallisation from ethanol-water, followed by drying, gave the title compound (1.35 g), melting point 194°–5° C.

Analysis: Found: C, 57.9%; H, 5.30%; N, 11.5%. C$_{23}$H$_{25}$F$_3$N$_4$O$_2$S requires C, 57.7%; H, 5.27%; N, 11.7%.

EXAMPLE 4

4-(8-Chloro-4-quinolinylamino)-N-[(1-ethyl-2-pyrrolidinyl methyl]benzenesulphonamide 4-(8-Chloro-4-quinolinyl)benzenesulphonyl chloride hydrochloride (7.9 g, 0.02 mol) was added portionwise to a well-stirred two-phase mixture of chloroform/water (200 ml/200 ml) containing sodium carbonate (21.0 g) and 2-aminomethyl-1-ethyl pyrrolidine (2.6 g, 0.02 mol) at about 10° C. The ice bath used for cooling was removed and after 1½ hours the mixture was separated. The chloroform layer was dried (MgSO$_4$) and evaporated under reduced pressure to give a dark brown solid. Purification was carried out by column chromatography (basic Al$_2$O$_3$ : 1% EtOH/CHCl$_3$) followed by trituration from ethyl acetate giving the title compound (2.2 g), melting point 171°-172.5° C. (dec).

Analysis: Found: C, 59.7%; H, 6.06%; N, 12.3%. C$_{22}$H$_{25}$ClN$_4$O$_2$S requires: C, 59.4%; H, 5.66%; N, 12.6%.

EXAMPLE 5

R-(+)-4-(7-Chloro-4-quinolinylamino)-N-[(1-ethyl-2-pyrrolidinyl) methyl]benzenesulphonamide 4-(7-Chloro-4-quinolinylamino)benzenesulphonyl chloride hydrochloride (4.3 g, 0.012 mol) was added portionwise to a well-stirred two phase mixture of water/chloroform (125 ml/125 ml) containing sodium carbonate (12.7 g) and R-(+)-2-aminomethyl-1-ethylpyrrolidine ditartrate (5.2 g, 0.012 mol), at about 10° C. The ice bath used for cooling was removed and after 1½ hours, the mixture was separated. The chloroform layer was dried (MgSO$_4$) and evaporated under reduced pressure to give a solid. Purification of the solid (8 g) was carried out by column chromatrography (basic Al$_2$O$_3$ : CHCl$_3$/1% EtOH) followed by recrystallisation from ethanol, to give the title compound (0.9 g), melting point 197°-199° C., [α]$_D^{16}$=+33° (c=0.90% in 95% ethanol).

Analysis: Found: C, 59.1%; H, 5.99%; N, 12.3%. C$_{22}$H$_{25}$ClN$_4$O$_2$S requires: C, 59.48%; H, 5.66%; N, 12.6%.

EXAMPLE 6

S-(-)-4-(7-Chloro-4-quinolinylamino)-N-[(1-ethyl-2-pyrrolidinyl)methyl]benzenesulphonamide 4-(7-Chloro-4-quinolinylamino)benzenesulphonyl chloride hydrochloride (14.2 g, 0.037 mol) was added portionwise to a well-stirred two phase mixture of water/chloroform (400 ml/400 ml) containing sodium carbonate (41.5 g) and S-(−)-2-aminomethyl-1-ethylpyrrolidine ditartrate (17.1 g, 0.04 mol), at about 10° C. The ice bath used for cooling was removed and after 1½ hours, the mixture was separated. The chloroform layer was dried (MgSO$_4$) and evaporated under reduced pressure to give a solid. Purification was carried out by column chromatography (basic Al$_2$)$_3$ : CHCl$_3$) followed by recrystallisation from ethanol/water, giving the title compound (0.6 g), melting point 194-197° C., [α]$_D^{21}$=−33° (c=1.21% in 95% ethanol). Analysis: Found: C, 59.2%; H, 5.82%; N, 12.4%. C$_{22}$H$_{25}$ClN$_4$O$_2$S requires: C, 59.4%; H, 5.66%; N, 12.6%.

EXAMPLE 7

4-(7-Chloro-4-quinolinylamino)-N-[(1-propyl-2-pyrrolidinyl) methyl]benzenesulphonamide 4-(7-Chloro-4-quinolinylamino)benzenesulphonyl chloride hydrochloride (5.4 g, 0.014 mol) was added portionwise to a well-stirred two phase mixture of chloroform/water (140 ml/140 ml) containing sodium carbonate (14.8 g) and 2-aminomethyl-1-propylpyrrolidine (2.0 g, 0.014 mol) at about 10° C. The mixture was allowed to warm to room temperature, then stirred for 1½ hours. The chloroform layer was separated, dried (MgSO$_4$) and evaporated under reduced pressure to give a gum. The gum was crystallised from ethanol/water to give a pale yellow solid (1.8 g). A further recrystallisation from ethanol gave the title compound (0.5 g), melting point 192.5°-194° C.

Analysis: Found: C, 60.0%; H, 5.66%; N, 12.0%. C$_{23}$H$_{27}$ClN$_4$O$_2$S requires: C, 60.2%; H, 5.93%; N, 12.2%.

EXAMPLE 8

4-(7-Chloro-4-quinolylamino)-N-[(1-acetyl-2-pyrrolidinyl) methyl]benzenesulphonamide The title compound is prepared in a similar manner to Example 1 by replacing 2-aminomethyl-1-ethylpyrrolidine by an equimolar amount of 1-acetyl-2-aminomethylpyrrolidine.

We claim:

1. A compound having the formula

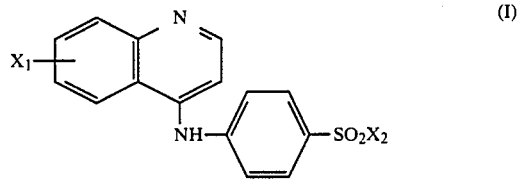

(I)

or a pharmaceutically acceptable salt thereof, wherein X$_1$ is selected from halogen and trifluoromethyl and X$_2$ represents a group having the formula

(II)

where Q is lower alkylene attached to a ring carbon atom of the ring illustrated in formula II; R$_1$ is selected from hydrogen and lower alkyl; and R$_4$ is lower alkyl and the ring illustrated in formula II is a piperidine or a pyrrolidine ring which is unsubstituted or substituted on one or more carbon ring members by a lower alkyl group.

2. A compound as claimed in claim 1, wherein X$_1$ in formula I substitutes the 7- position of the quinoline ring system.

3. A compound as claimed in claim 1, which is 4-(7-chloro-4-quinolylamino)-N-[(1-ethyl-2-piperidinyl) methyl]benzenesulphonamide or a pharmaceutically acceptable salt thereof.

4. A compound as claimed in claim 1, which is 4-(7-trifluoromethyl-4-quinolylamino)-N-[(1-ethyl-2-pyrrolidinyl)methyl]benzenesulphonamide or a pharamaceutically acceptable salt thereof.

5. A compound as claimed in claim 1, which is 4-(7-chloro-4-quinolylamino)-N-[(1-ethyl-2-pyrrolidinyl)-methyl]benzenesulphonamide or a pharmaceutically acceptable salt thereof.

6. A compound as claimed in claim 1, which is 4-(8-chloro-4-quinolylamino)-N-[(1-ethyl-2-pyrrolidinyl)-methyl]benzenesulphonamide or a pharmaceutically acceptable salt thereof.

7. A compound as claimed in claim 1, which is R-(+)-4-(7-chloro-4-quinolylamino)-N-[(1-ethyl-2-pyrrolidinyl)methyl]benzenesulphonamide or a pharmaceutically acceptable salt thereof.

8. A compound as claimed in claim 1, which is S-(−)-4-(7-chloro-4-quinolylamino)-N-[(1-ethyl-2-pyrrolidinyl)methyl]benzenesulphonamide or a pharmaceutically acceptable salt thereof.

9. A compound as claimed in claim 1, which is 4-(7-chloro-4-quinolylamino)-N-[(1-propyl-2-pyrrolidinyl)methyl]benzenesulphonamide or a pharmaceutically acceptable salt thereof.

10. A compound having the formula V

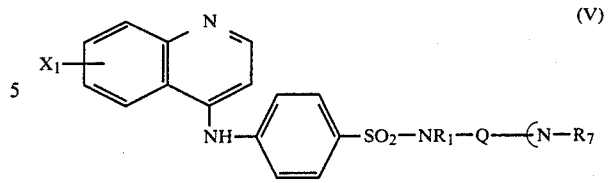

or a acid addition salt thereof, wherein $X_1$ is selected from halogen and trifluoromethyl; $R_1$ is selected from hydrogen and lower alkyl; Q is lower alkylene attached to a ring carbon atom of the ring illustrated; and $R_7$ is selected from hydrogen and lower alkanoyl and the ring illustrated is a piperidine or a pyrrolidine ring which is unsubstituted or substituted on one or more carbon ring members by a lower alkyl group.

11. A pharmaceutical composition useful as an antihypertensive agent comprising an effective amount of a compound as claimed in claim 1 in association or combination with a pharmaceutically suitable carrier.

* * * * *